United States Patent [19]

Meyer

[11] Patent Number: 5,185,473
[45] Date of Patent: Feb. 9, 1993

[54] PROCESS FOR THE PREPARATION OF PERFLUORINATED ETHERS

[75] Inventor: Matthias Meyer, Frankfurt am Main, Fed. Rep. of Germany

[73] Assignee: Hoechst Aktiengesellschaft, Frankfurt am Main, Fed. Rep. of Germany

[21] Appl. No.: 900,845

[22] Filed: Jun. 18, 1992

[30] Foreign Application Priority Data

Jun. 21, 1991 [DE] Fed. Rep. of Germany ....... 4120508

[51] Int. Cl.$^5$ .................. C07C 41/01; C07C 43/02
[52] U.S. Cl. ............................ 568/615; 568/613; 568/614
[58] Field of Search ............... 568/613, 614, 615

[56] References Cited

U.S. PATENT DOCUMENTS 3,242,218  3/1966  Miller ............................... 568/615
3,555,100  1/1971  Garth et al. ....................... 568/615

FOREIGN PATENT DOCUMENTS 0154297  9/1985  European Pat. Off. ............ 568/615
0167258  2/1989  European Pat. Off. ............ 568/615
2451493  10/1974  Fed. Rep. of Germany ...... 568/615
0164535  7/1983  Japan ................................ 568/615
0006813  11/1987  World Int. Prop. O. .

OTHER PUBLICATIONS

Nippon, "Chemical Abstracts", vol. 95, (1981) p. 95:25879t.

Primary Examiner—Werren B. Lone

[57] ABSTRACT

The invention relates to a process for the preparation of perfluorinated ethers of the formula $R-CF_2-CF_3$, in which R is the radical $CF_3(CF_2)_2-O-[-CF(CF_3)CF_2-O]_n-$, in which n is an integer from 0 to 60, by decarbonylation of perfluoroether-acyl fluorides of the formula $R-CF(CF_3)-COF$ at 150°–350° C. in the presence of $AlCl_3$ and/or $AlBr_3$.

5 Claims, No Drawings

PROCESS FOR THE PREPARATION OF PERFLUORINATED ETHERS

The invention relates to a process for the preparation of perfluorinated ethers of the formula (I)

$$R-CF_2-CF_3 \qquad (I)$$

in which R is the radical $CF_3(CF_2)_2-O-[-CF(CF_3)CF_2-O]_n-$, in which n is an integer from 0 to 60, by decarbonylation of perfluoroether-acyl fluorides of the formula $R-CF(CF_3)-COF$.

Perfluoroethers of the formula (I) are distinguished by a high heat stability, and they are non-combustible and chemically stable, even against attacks by powerful oxidizing agents.

Because of their particular physical properties, in particular favorable viscosity properties within wide temperature ranges, high boiling points coupled with simultaneously low pour points, low surface tension and extreme dielectric properties, perfluorinated polyethers find diverse uses as inert liquids, dielectrics, heat exchange media, hydraulic oils and lubricants in the presence of highly aggressive media.

The oligomerization of hexafluoropropene oxide (HFPO) in the presence of CsF and polyethylene glycol dimethyl ethers, in particular tetraethylene glycol dimethyl ether, is described in EP-A-0 154 297. The crude oligomer is in general obtained here as a mixture having a molecular weight distribution of about 300–20,000 g/mol. It consists of perfluoroether-acyl fluorides of the formula $R-CF(CF_3)COF$, in which R has the above-mentioned meaning, but the compounds are still contaminated with CsF and the polyethylene glycol dimethyl ether employed as the solvent.

The acyl fluorides mentioned are sensitive to hydrolysis, aggressive and toxic fluorinated fragments split off at a high temperature, and they therefore cannot be employed as inert liquids.

Various methods are known for "end group stabilization" of these acyl fluorides, i.e. conversion into perfluorinated ethers.

According to EP-A-0 154 297, the acyl fluorides are hydrolyzed to carboxylic acids, these are converted into the salts and these salts are then decarboxylated in the presence of alkaline media. However, only incompletely fluorinated ethers of the formula $R-CHFCF_3$ are obtained by this route.

It is furthermore known from U.S. Pat. No. 3,242,218 that the carboxylic acids corresponding to the acyl fluorides can be subjected to decarboxylating fluorination with elemental fluorine. In this reaction, the carboxyl group is replaced by a fluorine atom in accordance with the equation $$R-CF(CF_3)COOH + F_2 \rightarrow R\ CF_2CF_3 + CO_2 + HF$$

In this process, it is necessary first to hydrolyze the acyl fluorides obtainable according to EP-A-0 154 297 and to dry the carboxylic acids prepared thoroughly, before the reaction with fluorine is carried out. Hydrogen fluoride is obtained as a by-product both of the hydrolysis and of the fluorination.

German Offenlegungsschrift 2 451 493 describes the direct fluorination of acyl fluorides with elemental fluorine to give perfluorinated ethers in the presence of Ag/Cu catalysts in accordance with the following equation:

$$R-CF(CF_3)COF + F_2 \rightarrow R-CF_2CF_3 + COF_2$$

According to U.S. Pat. No. 3,555,100, the acyl fluorides are decarbonylated directly—without prior hydrolysis—in the presence of antimony pentafluoride to give perfluoroethers of the formula (I). However, side reactions with antimony pentafluoride lead to fragmentation products, which reduce the yield. The residence time of the reaction partners is critical, especially at higher temperatures, and is to be kept as short as possible. Furthermore, antimony pentafluoride and its secondary products formed in the side reaction must be separated off after the reaction. This requires aqueous working up, with destruction of the valuable $SbF_5$ catalyst. In addition, waste water problems arise, and the perfluoroethers furthermore have to be dried.

It is reported in Chemical Abstracts Volume 95 (1981) 25879t that the acyl fluorides can be decarbonylated with equal parts by weight of $AlF_3$ at high temperatures to give the perfluoroethers of the formula (I). One disadvantage of this process is the large amount of $AlF_3$ employed. Fragmentation reactions are furthermore to be expected at the reaction temperatures of 300°–320° C. described. Such a fragmentation of acyl fluorides of the formula $R-CF(CF_3)COF$ with $AlF_3$ is described in EP-A-0 167 258.

The invention relates to a process for the preparation of perfluorinated ethers of the formula (I)

$$R-CF_2-CF_3 \qquad (I)$$

in which R is the radical $CF_3(CF_2)_2-O-[-CF(CF_3)CF_2-O]_n-$, in which n is an integer from 0 to 60, by decarbonylation of perfluoroether-acyl fluorides of the formula $R-CF(CF_3)-COF$, in which R has the meaning given, which comprises carrying out the decarbonylation at 150°–350° C. in the presence of $AlCl_3$ and/or $AlBr_3$.

The acyl fluorides are heated to the reaction temperature with $AlCl_3$ and/or $AlBr_3$ in, for example, a stirred flask under an inert gas atmosphere.

Preferably, however, the acyl fluoride is initially introduced into the flask and is heated, and $AlCl_3$ and/or $AlBr_3$ are then added. No solvent is necessary.

The amounts of $AlCl_3$ and/or $AlBr_3$ added are in general 1–100 mol %, based on the acyl fluoride employed, preferably 3–10 mol %.

The reaction temperature is 150°–350° C., preferably 200°–280° C., in particular 240°–260° C.

Acyl fluorides of the general formula $R-CF(CF_3)COF$, in which n is an integer from 0 to 60, are employed. The value of n can be controlled by the temperature during the oligomerization of HFPO in accordance with EP-A-0 154 297. The lower the temperature chosen, the higher the value of n. Values of $n=10$ to $n=60$ are of particular interest. However, a mixture of acyl fluorides is always formed. Such a mixture is in general employed in the process according to the invention. However, it is also possible for an individual acyl fluoride first to be isolated therefrom by rectification and then to be employed.

Before the acyl fluorides are employed in the process according to the invention, the crude HFPO oligomer obtained according to EP-A-0 154 297 is first freed from the cesium fluoride and tetraethylene glycol dimethyl ether contained therein as a result of the preparation, since these compounds can undergo undesirable side reactions with the aluminum halides. This purification is achieved by extraction with a non-polar, aprotic solvent, subsequent phase separation and removal of the CsF from the acyl fluoride phase by filtration.

The reaction of the acyl fluorides with $AlCl_3$ and/or $AlBr_3$ can be monitored by IR and $^{19}F$-NMR spectroscopy, and has ended when the carbonyl band at about 1890 $cm^{-1}$ in the IR spectrum has disappeared and the signals of the $CF(CF_3)COF$ end group of the acyl fluorides are no longer visible in the $^{19}F$-NMR spectrum.

When the reaction has ended, the product is separated off from the $AlCl_3$ and/or $AlBr_3$ solid by filtration. The water-clear, colorless filtrate can be passed for fractionation into boiling ranges by flash distillation without further purification steps.

EXAMPLES

Test report

Preparation of the acyl fluorides of the formula R—CF(CF₃)COF according to EP-A-0 154 297.

A solution of 20 g of CsF in 50 ml of tetraethylene glycol dimethyl ether (tetraglyme) and 56 g of hexafluoropropylene oxide were initially introduced into a 4 l V-4-A autoclave under a nitrogen atmosphere. 250 ml of ®Frigen F113 were additionally added for dilution. 4000 g of hexafluoropropylene oxide were then passed in at a temperature of $-5°$ C. over a period of 8 hours, while mixing thoroughly. When the reaction had ended, the mixture was warmed to room temperature and the crude oligmer was discharged under an $N_2$ atmosphere. The acyl fluoride mixture which had been freed from the tetraglyme and CsF (by extraction with n-hexane, subsequent separation of the tetraglyme-containing hexane phase from the acyl fluoride phase and removal of the CsF from the acyl fluoride phase by filtration) was then employed in Example 1. Acyl fluoride mixtures were prepared analogously at temperatures of $-8°$ C. or $+5°$ C. for the Examples or 3 and 4 respectively.

EXAMPLE 1

580 g (=0.18 mol) of an acyl fluoride mixture having an average molecular weight of 3200 g/mol were heated to 250° C. under an $N_2$ atmosphere, after addition of 0.8 g of anhydrous aluminum chloride (0.006 mol). When a temperature of 200° C. was reached, gentle evolution of CO started. The reaction was monitored by $^{19}F$-NMR and IR spectroscopy, and had ended after about 5 hours. After the $AlCl_3$ solid had been removed by filtration, 493 g of perfluoroether of the formula (I) were obtained.

EXAMPLE 2

3657 g (=0.9 mol) of acyl fluoride mixture having an average molecular weight of 4100 g/mol (prepared at $-8°$ C.) were heated to 300° C. under an $N_2$ atmosphere. When this temperature had been reached, 12 g of anhydrous aluminum chloride (0.09 mol) were added in portions. Vigorous evolution of gas started after each addition of $AlCl_3$. The reaction was monitored by $^{19}F$-NMR and IR spectroscopy and had ended after 3 hours. After filtration, 3330 g of product of the formula (I) having an average molecular weight of 3900 g/mol were obtained.

EXAMPLE 3

0.15 mol of anhydrous $AlCl_3$ was added to 1900 g (=1.3 mol) of an acyl fluoride mixture having an average molecular weight of 1460 g/mol (prepared at $+5°$ C.) and the mixture was heated to 225° C. The reaction was monitored by spectroscopy and had ended after 3 hours. After filtration, 1320 g of product of the formula (I) having an average molecular weight of 1250 g/mol were obtained.

EXAMPLE 4

The procedure was as in Example 3, but 35 g (=0.13 mol) of aluminum bromide (anhydrous) were added instead of $AlCl_3$. The reaction had ended after 3.5 hours, and after filtration, 1480 g of product of the formula (I) having an average molecular weight of 1300 g/mol were obtained.

EXAMPLE 5

2 g of $AlCl_3$ (=0.015 mol) were added to 125 g (0.15 mol) of an acyl fluoride of the formula R—CF(CF₃)COF, where n=3 (obtained by distillation of an acyl fluoride mixture prepared at $+5°$ C.), and the mixture was heated to the boiling point (195° C.). After a reaction time of two hours, 60 g of a readily mobile liquid which, according to analysis by $^{19}F$-NMR, IR and gas chromatography, had the formula (I), where n=3, were distilled off from the reaction mixture over a column at 187° C. 50 g of the compound R—CF(CF₃)COCl, where n=3, were furthermore distilled over under reduced pressure at 100° C./13 mm Hg.

I claim:
1. A process for the preparation of a perfluorinated ether of the formula (I)

$$R-CF_2-CF_3 \qquad (I)$$

in which R is the radical $CF_3(CF_2)_2$—O—[—CF(CF₃)CF₂—O]$_n$—, in which n is an integer from 0 to 60, by decarbonylation of a perfluoroether-acyl fluoride of the formula R—CF(CF₃)—COF, in which R has the meaning given, which comprises carrying out the decarbonylation at 150°-350° C. in the presence of $AlCl_3$ and/or $AlBr_3$.

2. The process as claimed in claim 1, wherein 1-100 mol % of $AlCl_3$ and/or $AlBr_3$ is used, based on the perfluoroether-acyl fluoride employed.

3. The process as claimed in claim 1, wherein 3-10 mol % of $AlCl_3$ and/or $AlBr_3$ is used, based on the perfluoroether-acyl fluoride employed.

4. The process as claimed in claim 1, wherein the decarbonylation is carried out at 200°-280° C.

5. The process as claimed in claim 1, wherein the decarbonylation is carried out at 240°-260° C.

* * * * *